United States Patent [19]

Nishida

[11] Patent Number: 5,433,944
[45] Date of Patent: Jul. 18, 1995

[54] THERAPEUTIC AGENT FOR CORNEAL DISORDERS

[75] Inventor: Teruo Nishida, 27-14-106, Hinoikecho, Nishinomiya-shi, Hyogo, Japan

[73] Assignees: Santen Pharmaceutical Co., Ltd., Osaka; Teruo Nishida, Nishinomiya, both of Japan

[21] Appl. No.: 22,545

[22] Filed: Feb. 25, 1993

[30] Foreign Application Priority Data

Aug. 31, 1990 [JP] Japan .................................. 2-231954

[51] Int. Cl.$^6$ ..................... A61K 38/20; A61K 38/00; C07K 14/54
[52] U.S. Cl. ..................................... 424/85.2; 530/351
[58] Field of Search ......................... 530/351; 424/85.2

[56] References Cited

U.S. PATENT DOCUMENTS 5,300,292  4/1994  Ulich .................................. 530/351

FOREIGN PATENT DOCUMENTS

| | | |
|---|---|---|
| 0257406 | 2/1988 | European Pat. Off. . |
| 63-157996 | 6/1988 | Japan . |
| 3157996 | 6/1988 | Japan . |
| 64-63524 | 3/1989 | Japan . |
| 6463524 | 3/1989 | Japan . |
| 3007585 | 1/1991 | Japan . |
| WO88/00206 | 1/1988 | WIPO . |
| 8800206 | 1/1988 | WIPO . |
| WO90/01943 | 3/1990 | WIPO . |

OTHER PUBLICATIONS

Nishida, T. et al.; Ophthalmology 92:213–216, 1985.
Nishida, et al., Arch Ophthamol. vol. 101, Jul. 1985 pp. 1046–1051.
Droses et al., Annals of Rheumatic Diseases, vol. 45, pp. 732–735, 1986.
Behrens–Baumann, Acta Ophthalmalogica, vol. 70, pp. 690–692, 1992.
Portnoy et al., Cornea, vol. 10, No. 1, 1991, pp. 690–692.
Portnoy et al., Cornea vol. 10, No. 1, pp. 17–20, 1991.
Huang, A. J. Investigative Ophthalmology and Visual Science, vol. 32, No. 3, pp. 633–639, 1991.
Raqge et al., British Journal of Ophthalmology, vol. 74 pp. 381–382, 1990.
Klotz et al., Investigative Ophthalmology and Visual Science, vol. 30, No.6, Jun. 1989, pp. 1069–1074.
Archives of Ophthalmology, vol. 110, No. 9, Sep. 1992, pp. 1292–1294, Nishida et al., Interleukin 6 Facilitates Corneal Epithelial Wound Closure in Vitro.
The Journal of Investigative Dermatology, vol. 94, No. 6, Jun. 1990, pp. 2S–6S, Sehgal, P. B. et al., Interleukin-6: Molecular Pathophysiology.

*Primary Examiner*—Howard E. Schain
*Assistant Examiner*—Lynn Touzeau
*Attorney, Agent, or Firm*—Frishauf, Holtz, Goodman & Woodward

[57] ABSTRACT

A method for the healing of wounds caused by corneal injury as the result of, for example, corneal ulcer, corneal epithelial defect, keratitis, xerophthalmia, which comprises locally administering to a patient in need thereof an effective wound healing amount of interleukin-6, either alone, or in combination with one or more pharmaceutically acceptable ophthalmic excipients.

17 Claims, No Drawings

THERAPEUTIC AGENT FOR CORNEAL DISORDERS

This application is a continuation application of International application PCT/JP91/01130 filed Aug. 27, 1991 (Chapter II).

SPECIFICATION

1. Technical Field

The present invention relates to a therapeutic agent for corneal disorders comprising interleukin-6 as an active ingredient.

2. Background Art

Interleukin-6 has been known as an important physiologically active agent for the immune system, the hematopoietic system, etc.

However, research on the medical applications of interleukin-6 have been limited to its use in anti-cancer agents and in medicines for myeloid leukemia (WO Disclosure 88/00206, WO Disclosure 90/01943), and any ophthalmological effect thereof have not been known.

The inventor of the present invention conducted thorough research on the pharmacological effects of interleukin-6, particularly in the area of ophthalmology, and found that interleukin-6 is useful for treatment of corneal disorders.

DISCLOSURE OF THE INVENTION

The present invention relates to a therapeutic agent for corneal disorders comprising interleukin-6 as an active ingredient.

Examples of corneal disorders caused by various cornea damages are corneal ulcer, corneal epithelial defect, keratitis and xerophthalmia. Research is being conducted on various therapeutic drugs therefor.

The inventor of the present invention concentrated on the physiologically active substance interleukin-6 and its therapeutic effects on corneal disorders.

In order to investigate the therapeutic effects of interleukin-6 on corneal disorders, we studied its effect on corneal epithelial extension in vitro and its accelerating effect on the healing of corneal wounds in vivo.

Detailed data is given in the section on the pharmacological experiments. There was a clear extension of the corneal epithelial cell layer in the group to which interleukin-6 was added and a quicker healing of corneal wounds compared with the control group. These were evidence of the effectiveness of interleukin-6 as a therapeutic agent for corneal disorders.

The therapeutic agent for corneal disorders, according to the present invention, is to be preferably administered locally, particularly in the form of eyedrops.

The concentration of interleukin-6 in the eyedrop preparation may be determined depending on the symptoms, the age, etc. of the patient; however, it is preferably 0.00001–1%. The dosage may be, in the case of eyedrops, from 1 to several drops per use, from 1 to several times per day. The eyedrops may be a normally used in an eyedrop solution, or dissolved before using, or as an eye ointment. No special techniques are necessary for the preparation thereof, and the preparation may be made according to a conventional method, as necessary adding, for example, isotonizing agents such as sodium chloride and potassium chloride; buffers such as disodium hydrogen phosphate and sodium dihydrogen phosphate; stabilizers such as sodium edetate; preservatives such as ethylparaben, butylparaben and benzalkonium chloride; pH adjusting agents such as sodium hydroxide and diluted hydrochloric acid; and eye ointment bases such as white petrolatum and liquid paraffin.

Preferred Ways for the Invention

Preparation:

| 1) Eyedrop Formulation 1 (per 100 ml) | |
| --- | --- |
| Interleukin-6 | 0.01 g |
| Sodium chloride | 0.9 g |
| Sterilized purified water | q.s. |

Eyedrops can also be prepared in the same manner as Formulation 1, but containing 0.00001 g, 0.00003 g, 0.0001 g, 0.0005 g, 0.001 g, 0.005 g, 0.05 g and 0.1 g, respectively, of interleukin-6 per 100 ml.

| Formulation 2 (per 100 ml) | |
| --- | --- |
| Interleukin-6 | 0.1 g |
| Sodium chloride | 0.8 g |
| Disodium hydrogen phosphate | 0.1 g |
| Sodium dihydrogen phosphate | q.s. |
| Sterilized purified water | q.s. |

Eyedrops can also be prepared in the same manner as Formulation 2, but containing 0.00001 g, 0.00003 g, 0.0001 g, 0.0005 g, 0.001 g, 0.005 g, 0.01 g, 0.05 g, 0.5 g and 1.0 g, respectively, of interleukin-6 per 100 ml.

| 2) Eye ointment Formulation 3 (per 100 g) | |
| --- | --- |
| Interleukin-6 | 0.05 g |
| White petrolatum | 90 g |
| Liquid paraffin | q.s. |

Eye ointments can also be prepared in the same manner as Formulation 3, but containing 0.00001 g, 0.00003 g, 0.0001 g, 0.0005 g, 0.001 g, 0.005 g, 0.01 g, 0.1 g, 0.5 g and 1.0 g, respectively, of interleukin-6 per 100 g.

Pharmacological Experiment

In order to determine whether interleukin-6 is useful for the treatment of corneal disorders, we studied its effect on corneal epithelial extension in vitro and its accelerating effect on the healing of corneal wounds in vivo.

1) Effect on corneal epithelial extension in vitro

Method

The corneas of Japanese male white rabbits weighing 2.0–3.0 kg were used according to the method of Nishida et al. (The Journal of Cell Biology, 97, 1653, 1983).

Corneal blocks (6–8 per group) cut out from a section of rabbit cornea were cultured for 24 hours in a culture solution containing interleukin-6 (TC-199), and the extension of the corneal epithelial cells was measured.

The control group consisted of cells cultured in the same manner in a culture solution which contained none of the drug.

Result

The results are shown in Table 1.

TABLE 1

| Amount of Interleukin-6 added | Rate of cell extension with the control group defined as 1 |
|---|---|
| 1 ng/ml | 1.20 |
| 3 ng/ml | 1.22 |
| 10 ng/ml | 1.29 |

As shown in Table 1, the corneal epithelial cells cultured in the culture solution containing interleukin-6 were clearly observed to be extended in comparison with those in the control group, and the effect was dose-dependent on interleukin-6.

2) Accelerating effect on the healing of corneal wounds in vivo

Method

Japanese male white rabbits weighing 2.0–3.0 kg (one group of 7=14 eyes) were used. Corneal .epithelial defect was induced with n-heptanol, immediately after which dyeing with fluorescein was performed and a photograph of the cornea was taken. Eyedrops prepared by dissolving interleukin-6 in a vehicle [PBS(-)] as well as a preparation consisting of only the vehicle used for the control was instilled 4 times a day (50 µl/application) of 2 hours interval for 2 days. Twenty-four hours after the defect, fluorescein dyeing was conducted and a photograph of the cornea was taken. The area of the corneal wound was calculated by measuring the area of the fluorescein dyeing on the cornea seen in the photograph and using an image analysis processing system (Trade name: Cosmozone 1S, manufactured by Nikon, Inc.).

Result

The areas of the wounds (%) after 24 hours, with the area immediately after corneal epithelial defect defined as 100, are shown in Table 2.

TABLE 2

| Drug | Area of wound (%) |
|---|---|
| Control | 51.0 |
| Interleukin-6 | |
| 0.1 µg/ml | 39.7 |
| 0.3 µg/ml | 33.5 |
| 1.0 µg/ml | 30.5 |

In every case, the group to which interleukin-6 had been applied showed a decrease in the areas of the wounds in comparison to the control group, and the effect was dose-dependent on interleukin-6.

From the above results, it has become clear that interleukin-6 possesses an accelerating effect on the healing of wounds.

Industrial Applicability

The present invention provides a therapeutic agent for corneal disorders which comprises interleukin-6 as an active ingredient.

I claim:

1. A method for the healing of wounds caused by corneal injury which comprises administering to a patient in need thereof an effective wound-healing amount of interleukin-6.

2. The method of claim 1, wherein the interleukin-6 is locally administered and the corneal injury is a result of corneal ulcer, corneal epithelial defect, keratitis or xerophthalmia.

3. A method for the healing of wounds caused by cornea injury which comprises administering eyedrops to a patient in need thereof, said eyedrops comprising an effective wound-healing amount of interleukin-6 and one or more pharmaceutically effective ophthalmic excipients.

4. The method of claim 3, wherein the interleukin-6 is locally administered and the corneal injury is a result of corneal ulcer, corneal epithelial defect, keratitis or xerophthalmia.

5. The method of claim 4, wherein the interleukin-6 is in a concentration of 0.00001 to 1 weight %.

6. The method of claim 5, wherein the composition consists essentially of interleukin-6, sodium chloride and sterilized purified water.

7. The method of claim 5, wherein the composition consists essentially of interleukin-6, sodium chloride, disodium hydrogen phosphate, sodium dihydrogen phosphate and sterilized purified water.

8. A method for the healing of wounds caused by corneal injury which comprises administering a composition to a patient in need thereof, said composition comprising an effective wound-healing amount of interleukin-6 and one or more pharmaceutically acceptable ophthalmic excipients.

9. The method of claim 8, wherein the composition is in the form of an eye ointment.

10. The method of claim 9, wherein the interleukin-6 is locally administered and the corneal injury is a result of corneal ulcer, corneal epithelial defect, keratitis or xerophthalmia.

11. The method of claim 10, wherein the interleukin-6 is in a concentration of 0.00001 to 1 weight %.

12. The method of claim 11, wherein the composition consists essentially of interleukin-6, white petrolatum and liquid paraffin.

13. An eyedrop or eye ointment composition for the healing of wounds caused by corneal injury comprising an effective wound-healing amount of interleukin-6 and one or more pharmaceutically acceptable ophthalmic excipients.

14. The composition of claim 13, wherein the interleukin-6 is in a concentration of 0.00001 to 1 weight %.

15. The composition of claim 14, wherein the composition is an eyedrop composition which consists essentially of interleukin-6, sodium chloride and sterilized purified water.

16. The composition of claim 14, wherein the composition is an eyedrop composition which consists essentially of interleukin-6, sodium chloride, disodium hydrogen phosphate, sodium dihydrogen phosphate and sterilized purified water.

17. The composition of claim 14, wherein the composition is an eye ointment which consists essentially of interleukin-6, white petrolatum and liquid paraffin.

* * * * *